United States Patent
Jau et al.

(10) Patent No.: US 8,665,098 B2
(45) Date of Patent: Mar. 4, 2014

(54) NON-CONTACT MOTION DETECTION APPARATUS

(75) Inventors: Je-Kuan Jau, Tainan (TW); Ping-Hsun Wu, Kaohsiung (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 13/484,732

(22) Filed: May 31, 2012

(65) Prior Publication Data

US 2012/0235689 A1    Sep. 20, 2012

Related U.S. Application Data

(63) Continuation-in-part of application No. 12/886,522, filed on Sep. 20, 2010.

(30) Foreign Application Priority Data

Nov. 1, 2011   (TW) .............................. 100139869 A

(51) Int. Cl.
   *G08B 23/00*   (2006.01)
(52) U.S. Cl.
   USPC .................. 340/573.1; 340/571; 340/429
(58) Field of Classification Search
   USPC ............. 340/573.1, 573.6, 572.7, 571, 572.1, 340/572.5, 428–429
   See application file for complete search history.

(56) References Cited

U.S. PATENT DOCUMENTS

| | | |
|---|---|---|
| 3,221,260 A | 11/1965 | Henrion |
| 3,479,607 A | 11/1969 | Ruthroff |
| 4,517,982 A | 5/1985 | Shiga et al. |
| 4,600,890 A | 7/1986 | Horvat |
| 4,646,754 A | 3/1987 | Seale |
| 4,953,010 A | 8/1990 | Cowley |
| 4,958,638 A | 9/1990 | Sharpe et al. |

(Continued)

FOREIGN PATENT DOCUMENTS

| | | |
|---|---|---|
| CN | 101006915 | 8/2007 |
| CN | 101093995 | 12/2007 |

(Continued)

OTHER PUBLICATIONS

English language translation of abstract of CN 101006915 (published Aug. 1, 2007).

(Continued)

*Primary Examiner* — Daniel Previl
(74) *Attorney, Agent, or Firm* — McClure, Qualey & Rodack, LLP

(57) ABSTRACT

A non-contact motion detection apparatus includes at least one reception antenna, at least one transmission antenna, a voltage-controlled oscillator (VCO) and a phase lock loop (PLL). The at least one reception antenna receives a first wireless radio frequency (RF) signal. The at least one transmission antenna transmits a second wireless RF signal to an object which reflects the second wireless RF signal into the first wireless RF signal. The VCO outputs an oscillation signal to the at least one transmission antenna. The first wireless RF signal received by the at least one reception antenna is injected to the VCO. The PLL generates a control voltage to the VCO according to the oscillation signal from the VCO and a reference frequency. Controlled by the control voltage, which represents a motion information of the object, the oscillation signal of the VCO is locked to the reference frequency.

8 Claims, 2 Drawing Sheets

(56) References Cited

U.S. PATENT DOCUMENTS

| | | | |
|---|---|---|---|
| 4,991,585 | A | 2/1991 | Mawhinney |
| 5,458,124 | A | 10/1995 | Stanko et al. |
| 5,650,749 | A | 7/1997 | Main |
| 6,133,802 | A | 10/2000 | Ma |
| 6,369,647 | B1 | 4/2002 | Main et al. |
| 6,369,659 | B1 | 4/2002 | Delzer et al. |
| 7,103,132 | B1* | 9/2006 | Baba ............................ 375/376 |
| 7,740,588 | B1* | 6/2010 | Sciarra .......................... 600/484 |
| 8,147,409 | B2 | 4/2012 | Shifrin |
| 2006/0040739 | A1 | 2/2006 | Wells |
| 2007/0241864 | A1* | 10/2007 | Nagai ........................ 340/10.1 |
| 2008/0079636 | A1* | 4/2008 | Mohamadi ............ 343/700 MS |
| 2008/0146944 | A1 | 6/2008 | Tao et al. |
| 2008/0183053 | A1 | 7/2008 | Borgos et al. |
| 2009/0278728 | A1* | 11/2009 | Morgan et al. ................ 342/115 |
| 2010/0152600 | A1 | 6/2010 | Droitcour et al. |
| 2010/0198083 | A1 | 8/2010 | Lin et al. |
| 2010/0249630 | A1 | 9/2010 | Droitcour et al. |
| 2010/0259305 | A1 | 10/2010 | Lee et al. |

FOREIGN PATENT DOCUMENTS

| | | |
|---|---|---|
| EP | 2180593 A1 | 4/2010 |
| TW | 200901940 A | 1/2009 |
| TW | 201120790 | 6/2011 |
| TW | 1347108 | 8/2011 |

OTHER PUBLICATIONS

English language translation of abstract of CN 101093995 (published Dec. 26, 2007).

English language translation of abstract of TW 201120790 (published Jun. 16, 2011).

English language translation of abstract of TW 1347108 (published Aug. 11, 2011).

Fletcher, R., et al.; "Low-Cost Differential Front-End for Doppler Radar Vital Sign Monitoring;" IEEE; 2009; pp. 1325-1328.

Main, E., et al.; "FM Demodulation Using an Injection-Locked Oscillator;" IEEE; 2000; pp. 135-138.

Biswas, B.N., et al.; "A Doubly Tracking Discriminator;" IEEE; 2009; pp. 1-4.

Tarar, M., et al.; "Injection-Locked Phase-Locked Loop for BPSK Coherent Demodulation: Theory and Design;" IEEE 2007; pp. 387-390.

Chattopadhyay, T., et al.; "A New Microwave Discriminator;" IEEE; 2003; pp. 1078-1081.

Chattopadhyay, T.P., et al.; "Improved X-Band FM Discriminator;" IEEE Transactions on Microwave Theory and Techniques; vol. MTT-34; No. 4; Apr. 1986; pp. 442-446.

Non-Final Office Action issued for U.S. Appl. No. 13/456,849, filed Apr. 26, 2012 mailed Oct. 17, 2013.

TW Office Action dated Dec. 16, 2013.

\* cited by examiner

NON-CONTACT MOTION DETECTION APPARATUS

This is a continuation-in-part application of U.S. application Ser. No. 12/886,522, filed Sep. 20, 2010, which claims the benefit of Taiwan application Serial No. 100139869, filed Nov. 1, 2011. The disclosure of which is incorporated by reference herein in its entirety.

TECHNICAL FIELD

The disclosure relates in general to a non-contact motion detection apparatus.

BACKGROUND

In recent years, as people's living standards are greatly improved, people are more concerned with their health. Since many people may neglect their body warning messages, a number of vital sign measuring devices are provided for monitoring the vital signs of people so that people are aware of their health.

Currently, there are two types of vital sign sensing apparatuses, namely, contact type and non-contact type. The contact vital sign sensing apparatus performs measurement by touching people's body and has simple circuit constitution. However, people may feel uncomfortable if the contact vital sign sensing apparatus contacts his/her skin for a long time. In comparison to the contact vital sign sensing apparatus, the non-contact vital sign sensing apparatus reduces the people's uneasiness during sensing.

Therefore, the present disclosure provides a non-contact motion detection apparatus, which detects the chest heaving of people in a non-contact manner, and further obtains user physiological parameters (such as the frequencies of breathing and heartbeat) or other external motion information. The non-contact motion detection apparatus of the present disclosure is also used in motion detector or mechanical vibration frequency detecting.

SUMMARY

The disclosure is directed to a non-contact motion detection apparatus which locks an output frequency of a voltage-controlled oscillator (VCO) with a phase lock loop (PLL). When external motion occurs (such as a chest heaving of a user body), the VCO output frequency tends to vary due to injection locking mechanism. The PLL adjusts the VCO control voltage in feedback loop for stabilizing the VCO output frequency, wherein the control voltage of the PLL represents the external motion information. The PLL has the functions of (1) fixing the output frequency and (2) frequency demodulation.

According to one embodiment, a non-contact motion detection apparatus including at least one reception antenna, at least one transmission antenna, a voltage-controlled oscillator (VCO), and a PLL is provided. The at least one reception antenna receives a first wireless RF signal. The at least one transmission antenna transmits a second wireless RF signal to an object under measurement which reflects the second wireless RF signal into the first wireless RF signal. The VCO is coupled to the at least one reception antenna and the at least one transmission antenna for outputting an oscillation signal to the at least one transmission antenna, wherein the first wireless RF signal received by the at least one reception antenna is injected to an injection end of the VCO. The PLL generates a control voltage to the VCO according to the oscillation signal generated by the VCO and a reference frequency. Under controlled by the control voltage, the oscillation signal of the VCO is locked to the reference frequency. The control voltage represents a motion information of the object under measurement.

According to another embodiment, a non-contact motion detection apparatus including at least one antenna, a VCO, and a PLL is provided. The at least one antenna receives a first wireless RF signal and transmits a second wireless RF signal. An object under measurement reflects the second wireless RF signal into the first wireless RF signal. The VCO is coupled to the at least one antenna for outputting an oscillation signal to the at least one antenna, wherein the first wireless RF signal received by the at least one antenna is injected to the VCO. The PLL generates a control voltage to the VCO according to the oscillation signal generated by the VCO and a reference frequency. Under controlled by the control voltage, the oscillation signal of the VCO is locked to the reference frequency. The control voltage represents a motion information of the object under measurement.

It is to be understood that both the foregoing general description and the following detailed description are exemplary and explanatory only and are not restrictive of the disclosed embodiments, as claimed.

Figure 1:
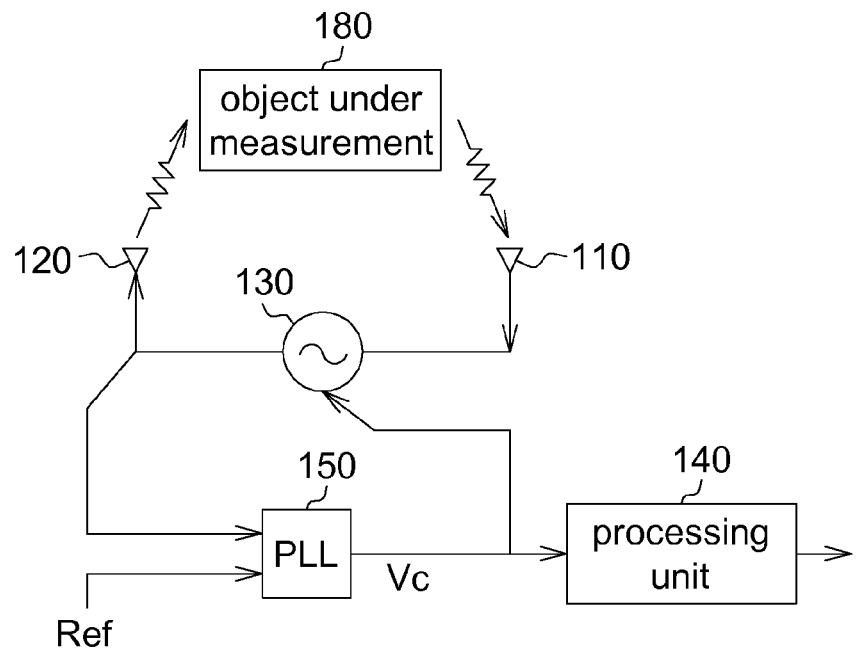
FIG. 1 shows a block diagram of a non-contact motion detection apparatus according to an embodiment of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION

Besides of sensing vital signs, a non-contact motion detection apparatus of the present disclosure may be used in motion detection or mechanical vibration frequency detection. As an exemplification of the present disclosure, the non-contact motion detection apparatus is used for sensing vital signs but the disclosure is not limited to such exemplification.

In embodiments of the disclosure, an output frequency of a voltage-controlled oscillator (VCO) may vary if the VCO is affected by external interference. Therefore, physiological parameters or motion parameters of an object under measurement are obtained from the variation in the VCO output frequency.

Since the Doppler Effect is caused by the chest heaving of a body and drifts the VCO output frequency, in embodiments of the disclosure, a phase lock loop (PLL) is used to lock the VCO output frequency to prevent the output frequency from drifting. Since a control voltage from the PLL represents variation information of the VCO output frequency, the control voltage from the PLL thus represents the vital sign of a body.

The non-contact motion detection apparatus of one embodiment of the disclosure detects physiological parameters such as breathing frequency or heartbeat frequency in a non-contact manner.

In one embodiment of the disclosure, the VCO is used as a detection element, and the chest heaving of the object under measurement will be reflected in the variation in VCO output frequency.

In one embodiment of the disclosure, the PLL suppresses variation in VCO output frequency and demodulates the variation in VCO output frequency to obtain physiological parameters such as breathing frequency or heartbeat frequency of a user body.

FIG. 1 shows a block diagram of a non-contact motion detection apparatus according to an embodiment of the disclosure. Referring to FIG. 1, the non-contact motion detection apparatus 100 includes signal antennas 110 and 120, a VCO 130, a processing unit 140 and a phase lock loop (PLL) 150.

The antenna 110 (such as a reception antenna) receives a first wireless signal (such as an RF modulation signal) to generate a first electrical signal.

The antenna 120 (such as a transmission antenna) is coupled to an output end of the VCO 130 to generate a second wireless signal to the object under measurement 180, and the object under measurement 180 reflects the first wireless signal to the antenna 110.

In the present embodiment of the disclosure, the object under measurement 180 is such as a user body, and parameters of the object under measurement 180 are physiological parameters such as heartbeat frequency, pulse and breathing frequency or motion signal (such as the body movement). Due to the Doppler Effect, the frequency of the first wireless signal is different from that of the second wireless signal.

The antenna 110 is coupled to an injection end of the VCO 130. That is, the first electrical signal received by the antenna 110 is injected to the injection end of the VCO 130. Interfered by the first electrical signal, the oscillation frequency of the VCO 130 is affected accordingly. The oscillation signal of the VCO 130 varies with the variation in the first electrical signal. In the present embodiment of the disclosure, if the VCO 130 is interfered by the first electrical signal, the VCO 130 activates its self-injection locking function so as to affect the frequency of the oscillation signal.

The processing unit 140 is coupled to the PLL 150 for evaluating parameters of the object under measurement 180 according to a control voltage Vc from the PLL 150.

The PLL 150 locks the VCO 130 according to a reference frequency Ref so as to lock the output frequency of the VCO 130 and to suppress frequency drifting. Thus, in principle the occupied band width is decreased.

Operations of the wireless sensing apparatus 100 are disclosed below. The antenna 120 transmits the second wireless signal to the object under measurement 180 (such as a user body) which reflects the second wireless signal as the first wireless signal to the antenna 110. In the present embodiment of the disclosure, due to breathe, heartbeat, pulse or body movement, a Doppler effect is generated by the second wireless signal and breathe/heartbeat/pulse/body movement. Therefore, the frequency of the first wireless signal reflected by the body is different from the frequency of the second wireless signal transmitted from the antenna 120.

The antenna 110 receives the first wireless signal and accordingly generates the first electrical signal to the VCO 130, and the VCO 130 generates an oscillation signal to the PLL 150, wherein the frequency of the oscillation signal is the same with that of the first electrical signal. The PLL 150 generates the control voltage Vc according to a frequency difference and/or a phase difference between the oscillation signal and the reference frequency Ref, wherein the control voltage Vc adjusts the output oscillation frequency of the VCO 130 as being consistent with the reference frequency Ref. Information such as the body's heartbeat, breathing, pulse or other motion may be obtained from the control voltage Vc outputted by the PLL 150. The control voltage Vc controls and locks the output oscillation frequency of the VCO 130.

That is, the oscillation signal of the VCO 130 represents information such as the heartbeat, breathing, pulse or other body motion (that is, parameters of the object under measurement 180). The oscillation signal is demodulated into the control voltage Vc by the PLL 150. The processing unit 140 processes the control voltage Vc to obtain information such as the body's heartbeat, breathing, pulse or other motion information.

In the present embodiment of the disclosure, the output port of the VCO 130 is used as a signal transmission end, and the oscillation signal outputted from the output port is sent out as a wireless carrier signal by the antenna 120. If the wireless carrier signal is reflected by the object under measurement 180, the reflected signal (from the object under measurement 180) affected by the Doppler Effect is received by the antenna 110 and inputted/injected to the VCO 130. The VCO 130 is affected by the injected signal.

In the present embodiment of the disclosure, the PLL 150 locks the output oscillation signal of the VCO 130. When external motion affects the VCO 130, the PLL 150 adjusts the control voltage Vc applied to the VCO 130 in negative feedback, for stabilizing the output oscillation frequency of the VCO 130. The control voltage Vc generated by the PLL 150 represents information of external motion. That is, in the present embodiment of the disclosure, the PLL 150 at least has functions of (1) fixing the output oscillation frequency of the VCO 130 and (2) frequency demodulation.

In the present embodiment of the disclosure, the processing unit 140 may such as include an analog-to-digital converter and a digital signal processor. The analog-to-digital converter performs analog-to-digital conversion on the control voltage outputted from the PLL 150 into a digital signal. The digital signal processor is coupled to the analog-to-digital conversion unit for processing the digital signal generated by the analog-to-digital converter into results which represent the parameters of the object under measurement 180.

Figure 2A:
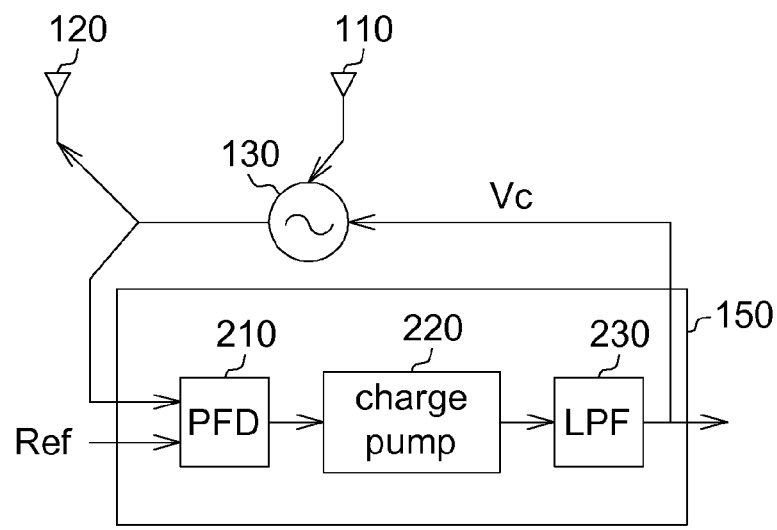
FIG. 2A and FIG. 2B show functional block diagrams of two possible implementations of a PLL according to an embodiment of the disclosure.
Figure 2B:
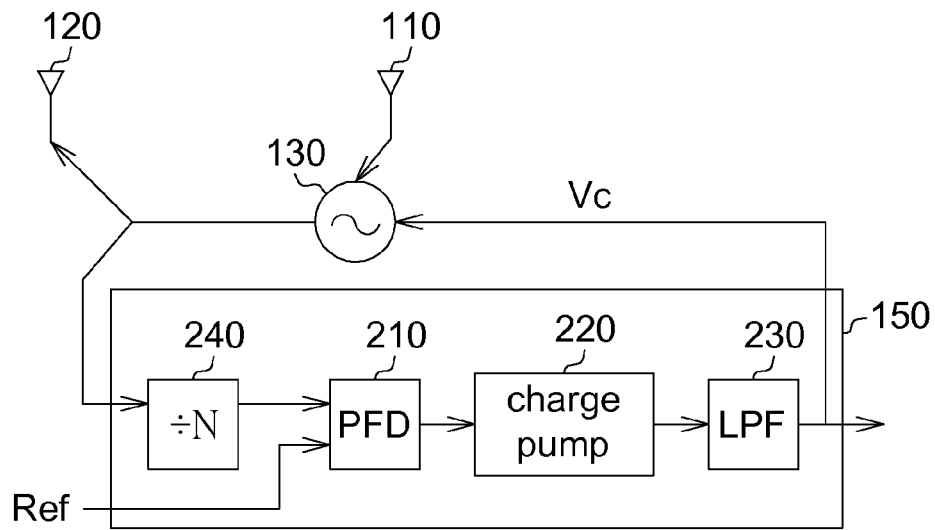

Referring to FIG. 2A and FIG. 2B, functional block diagrams of two possible implementations of the PLL 150 according to an embodiment of the disclosure are shown.

As indicated in FIG. 2A, the PLL 150 includes a phase frequency detector (PFD) 210, a charge pump 220 and a low-pass filter (LPF) 230.

The output signal of the VCO 130 and the local reference frequency Ref are received by the phase frequency detector (PFD) 210. An output voltage signal of the PFD 210 represents a phase difference or a frequency difference between the output signal of the VCO 130 and the local reference frequency Ref. The output voltage signal of the PFD 210 is inputted to the charge pump 220 and converted into a current signal. High-frequency signal of the current signal is filtered by the low-pass filter 230 into the analog voltage signal Vc. The analog voltage signal Vc is inputted to the control end of the VCO 130 for controlling oscillation of the VCO 130. The PLL 150 has a negative feedback loop, and under control of the analog voltage signal Vc, the VCO output frequency tracks the frequency of the reference frequency Ref.

When the reflected signal affected by the Doppler Effect is injected to the VCO 130 and makes the frequency of the VCO 130 drift, the VCO 130 is locked by the PLL 150 and fixed to the reference frequency Ref. Therefore, the control voltage Vc input into the control end of the VCO 130 reflects the frequency drifting, and a voltage variation opposite to the frequency drifting is generated. In the present embodiment of the disclosure, information of external motion is obtained from the control voltage Vc input into the control end of the VCO 130. Besides, since the locking speed of the PLL 150 is usually much quicker than physical motion of the target under detection, the output frequency of the VCO 130 is fixed to the reference frequency.

In FIG. 2B, another implementation of the PLL 150 further includes a frequency divider 240 which divides the frequency of the output oscillation signal of the VCO 130 and then outputs the frequency-divided signal to the PFD 210. The PFD 210 compares the frequency-divided oscillation signal with the reference frequency Ref. The remaining operations are similar to FIG. 2A, and the details are omitted here.

Figure 3:
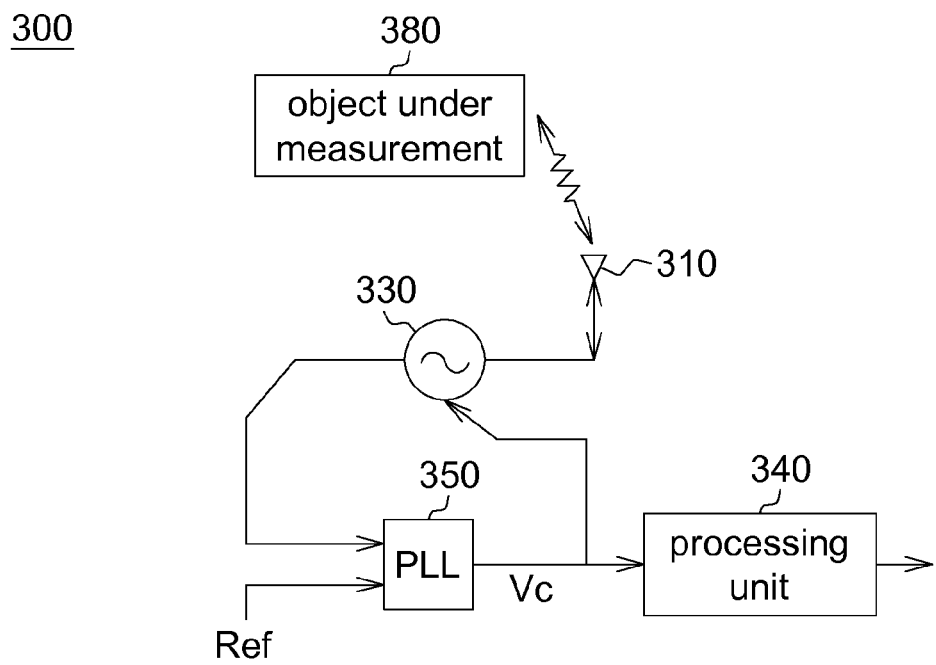
FIG. 3 shows a block diagram of a non-contact motion detection apparatus according to another embodiment of the disclosure.

FIG. 3 shows a block diagram of a non-contact motion detection apparatus according to another embodiment of the disclosure. Referring to FIG. 3, the non-contact motion detection apparatus 300 includes an antenna 310, a VCO 330, a processing unit 340 and a PLL 350.

In the present embodiment, the antenna 310 has functions of receiving and transmitting wireless signals. An output oscillation signal of the VCO 330 is transmitted to an object under measurement 380 through the antenna 310 and reflected by the object under measurement 380. The reflected signal is injected to the VCO 330 via the antenna 310.

The function and structure of the PLL 350 are the same with or similar with that the PLL 150 of FIG. 1 and the details are omitted here. For example, functional blocks of the PLL 150 of FIG. 2A and FIG. 2B are applicable for implementing the PLL 350 of FIG. 3.

By detecting physiological parameters or motion information of an object under measurement, the above two embodiments of the disclosure may be used in security application, remote Medicare application, sport application and fitness equipment application, homecare application, speed sensing application and action sensing application.

Since the VCO, the PLL and the processing unit may be realized by transistors and integrated circuits, the above two embodiments of the disclosure could have the advantage of integration.

In the above two embodiments of the disclosure, the PLL controls the VCO and makes the output oscillation signal of the VCO fixed, so the output oscillation signal of the VCO is free of drifting problem and the occupied frequency band width is smaller. In convention, the frequency bandwidth occupied by prior systems increases as the sensitivity of the VCO increases. This is because the transmission carrier drifts due to external motion. The drift is demodulated into physiological parameters. However, if the sensitivity of the VCO increases, frequency drift also increases accordingly, and a larger channel bandwidth is needed in principle.

In the above embodiments, the reception antenna may include more than one antenna, and so is the transmission antenna.

It will be appreciated by those skilled in the art that changes could be made to the disclosed embodiments described above without departing from the broad inventive concept thereof. It is understood, therefore, that the disclosed embodiments are not limited to the particular examples disclosed, but is intended to cover modifications within the spirit and scope of the disclosed embodiments as defined by the claims that follow.

What is claimed is:

1. A non-contact motion detection apparatus, comprising:
at least one reception antenna for receiving a first wireless radio frequency (RF) signal;
at least one transmission antenna for transmitting a second wireless RF signal to an object under measurement which reflects the second wireless RF signal into the first wireless RF signal;
a voltage-controlled oscillator (VCO) coupled to the at least one reception antenna and the at least one transmission antenna, for outputting an oscillation signal to the at least one transmission antenna, wherein the first wireless RF signal received by the at least one reception antenna is injected to the VCO; and
a phase lock loop (PLL) for generating a control voltage into the VCO according to the oscillation signal generated by the VCO and a reference frequency,
wherein under controlled by the control voltage, the oscillation signal of the VCO is locked to the reference frequency and the control voltage represents a motion information of the object under measurement.

2. The non-contact motion detection apparatus according to claim 1, wherein due to a Doppler effect generated by the motion information, a frequency of the second wireless RF signal is different that of the first wireless RF signal.

3. The non-contact motion detection apparatus according to claim 1, further comprising:
a processing unit coupled to the VCO and the PLL for evaluating the motion information of the object under measurement according to the control voltage of the PLL.

4. The non-contact motion detection apparatus according to claim 1, wherein the motion information of the object under measurement comprises a physiological parameter.

5. A non-contact motion detection apparatus, comprising:
at least one antenna for receiving a first wireless RF signal and transmitting a second wireless RF signal, an object under measurement reflecting the second wireless RF signal into the first wireless RF signal;
a VCO coupled to the at least one antenna for outputting an oscillation signal to the at least one antenna, wherein the first wireless RF signal received by the at least one antenna is injected to the VCO; and
a PLL for generating a control voltage to the VCO according to the oscillation signal generated by the VCO and a reference frequency,
wherein controlled by the control voltage, the oscillation signal of the VCO is locked to the reference frequency and the control voltage represents a motion information of the object under measurement.

6. The non-contact motion detection apparatus according to claim 5, wherein due to a Doppler effect generated by the motion information, a frequency of the second wireless RF signal is different that of the first wireless RF signal.

7. The non-contact motion detection apparatus according to claim 5, further comprising:
a processing unit coupled to the VCO and the PLL for evaluating the motion information of the object under measurement according to the control voltage of the PLL.

8. The non-contact motion detection apparatus according to claim 5, wherein the motion information of the object under measurement comprises a physiological parameter.

* * * * *